(12) United States Patent
Balashanmugam et al.

(10) Patent No.: US 10,344,229 B2
(45) Date of Patent: Jul. 9, 2019

(54) PREDICTING HIGH TEMPERATURE ASPHALTENE PRECIPITATION

(71) Applicant: BP Corporation North America Inc., Houston, TX (US)

(72) Inventors: Soban Balashanmugam, Surrey (GB); Ronald Fisher, San Antonio, TX (US); Devin Halliday, Chicago, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 15/239,034

(22) Filed: Aug. 17, 2016

(65) Prior Publication Data

US 2017/0058217 A1 Mar. 2, 2017

Related U.S. Application Data

(60) Provisional application No. 62/212,790, filed on Sep. 1, 2015.

(51) Int. Cl.
*C10G 75/00* (2006.01)
*C10G 75/04* (2006.01)
*G01N 17/00* (2006.01)
*G01N 33/28* (2006.01)

(52) U.S. Cl.
CPC ............. *C10G 75/04* (2013.01); *C10G 75/00* (2013.01); *G01N 17/008* (2013.01); *G01N 33/2823* (2013.01)

(58) Field of Classification Search
CPC .............................. C10G 75/00; G01N 17/008
See application file for complete search history.

(56) References Cited

U.S. PATENT DOCUMENTS

| 4,671,103 A * | 6/1987 | Dickakian .......... G01N 33/2823 210/656 |
| 4,853,337 A * | 8/1989 | Dickakian ................. C10L 1/00 208/14 |
| 5,871,634 A * | 2/1999 | Wiehe .................... C10G 9/005 208/48 R |
| 7,618,822 B2 * | 11/2009 | Nemana ................. C10G 75/00 436/139 |
| 2004/0121472 A1 | 6/2004 | Nemana et al. |

FOREIGN PATENT DOCUMENTS

EP 0 241 233 10/1987
WO WO 2011/113017 9/2011

* cited by examiner

*Primary Examiner* — Randy Boyer
(74) *Attorney, Agent, or Firm* — Kalim S Fuzail (57) ABSTRACT

A method for determining a relationship between the ratio of solvent power to critical solvent power and the threshold light paraffin content of a hydrocarbon fluid is provided. The method comprises:
  dividing the plurality of hydrocarbon fluids into subgroups, based on the ratio of solvent power to critical solvent power;
  for each of the subgroups, determining the threshold light paraffin content, said threshold light paraffin content being the light paraffin content of the hydrocarbon fluids at the point at which the fouling tendency of the hydrocarbon fluids exceeds a fouling threshold; and
  determining a relationship between the ratio of solvent power to critical solvent power and the threshold light paraffin content.

16 Claims, 4 Drawing Sheets

PREDICTING HIGH TEMPERATURE ASPHALTENE PRECIPITATION

FIELD OF THE INVENTION

The present invention relates to methods for predicting asphaltene precipitation from a hydrocarbon fluid at high temperatures. In particular, the present invention relates to methods for predicting asphaltene precipitation from a fluid that is used as the feed stream to a refinery.

BACKGROUND OF THE INVENTION

Heavy crude oils typically contain asphaltenes. Asphaltenes are organic heterocyclic macro-molecules that usually represent the heaviest compounds in crude oil. Asphaltenes are defined as a solubility class and, whilst they are typically soluble in aromatic solvents such as toluene, they are insoluble in paraffinic solvents such as n-heptane.

Under normal conditions (i.e. atmospheric temperature and pressure), the asphaltenes in a crude oil are generally stable and remain in solution. However, during refining, crude oil is typically passed across a number of heat exchangers before being fed to the main Crude Distillation Unit (CDU). Generally, the crude oil will be subjected to a 'cold pre-heat' which involves passing the crude oil across a series of heat exchangers to bring it to an initial temperature of 90-140° C., followed by a desalting stage. The oil is then further heated in a bank of heat exchangers to a temperature of 230-270° C. This stage is known as the 'hot pre-heat'. The crude oil is then passed to a furnace for further heating before it is passed to the CDU.

During the entire cold and hot pre-heating stages, the crude oil undergoes thermal expansion. The solvent power of the crude oil is inversely related to the molar volume of the crude oil. Thus, as the crude oil undergoes thermal expansion, the molar volume increases and the solvent power drops. If the solvent power falls below the critical solvent power of the crude oil, asphaltenes in the crude oil become unstable and precipitation may be observed. As the precipitate begins to adhere to metal surfaces in the refinery, fouling occurs.

Furthermore, there is a gradual pressure drop throughout the pre-heating stages, and crude oil which started at a pressure of 30-60 bar is typically only at a pressure of 15-30 bar at the end of the pre-heating stages. A drop in pressure lowers the effective boiling point of the crude oil, exacerbating the effects of the thermal expansion.

Crude oil is typically closest to its boiling point in the heat exchangers located immediately upstream of the furnace, and so the solvent power of the crude oil is at its lowest at this stage of the pre-heating process. Fouling rates therefore tend to be the highest in these heat exchangers.

Significant fouling is also observed in the furnace. However, once the crude oil has entered the furnace, components of the crude oil begin to vapourise. As components are evolved from the oil, the solvent power of the remaining liquid phase increases and asphaltene precipitation risks are generally lowered.

One of the biggest challenges faced by refineries that process crude oils is the ability to ensure that the asphaltenes in the crude oil are kept stable and in solution throughout the refinery.

Typical methods for assessing fouling risk of crude oils or blends thereof involve carrying out laboratory tests at atmospheric pressure and at temperatures of up to 60° C. These ambient condition lab measurements are used to generate compatibility parameters (i.e. solvent power and critical solvent power) from which the risk of asphaltene precipitation during crude oil processing may be predicted.

One method for reducing the risk of asphaltene precipitation is to ensure that the solvent power of a crude oil or a blend of crude oils is 5-15% higher than the critical solvent power (see US 2004/0121472).

However, high levels of fouling have been observed in crude oil blends which were believed to have an adequate margin between the solvent power and the critical solvent power, including crude oil blends with a ratio of solvent power to critical solvent power of greater than 1.30. Accordingly, a fixed margin between solvent power and critical solvent power is not, in some cases, enough to prevent unwanted asphaltene precipitation. Moreover, the margin between the solvent power and the critical solvent of a crude oil blend can have implications for the economics of a refinery, as too high a margin can constrain the feedstocks that may be employed in the refinery. Whilst a suitable margin between solvent power and critical solvent power can be determined by trial and error, this can be costly in terms of time and equipment.

Accordingly, there is a need for an improved method for predicting the ratio of solvent power to critical solvent power at which asphaltene precipitation occurs, so as to avoid unexpected fouling in a refinery.

SUMMARY OF THE INVENTION

The present invention provides a method for determining a relationship between the ratio of solvent power to critical solvent power and the threshold light paraffin content of a hydrocarbon fluid, said method comprising:

dividing a plurality of hydrocarbon fluids into subgroups, based on the ratio of solvent power to critical solvent power;

for each of the subgroups, determining a threshold light paraffin content, said threshold light paraffin content being the light paraffin content of the hydrocarbon fluids at the point at which the fouling tendency of the hydrocarbon fluids exceeds a fouling threshold; and determining a relationship between the ratio of solvent power to critical solvent power and the threshold light paraffin content.

The present invention further provides a method for determining whether a hydrocarbon fluid will exhibit an acceptable level of fouling, said method comprising:

(a) determining the ratio of solvent power to critical solvent power and the light paraffin content of the hydrocarbon fluid;

(b) based on the light paraffin content of the hydrocarbon fluid, predicting the ratio of solvent power to critical solvent power at which the hydrocarbon fluid will fall below a fouling threshold using a relationship determined using a method disclosed herein; and (c) comparing the ratio determined in step (a) with the ratio predicted in step (b) in order to determine whether the hydrocarbon fluid will exhibit an acceptable level of fouling.

Also provided is a method for reducing the precipitation of asphaltene from a hydrocarbon fluid in a refinery, said method comprising:

determining whether the hydrocarbon fluid will exhibit an acceptable level of fouling using a method disclosed herein; and if so, feeding the hydrocarbon fluid to the refinery and, if not, further blending the hydrocarbon fluid to increase the ratio of solvent power to critical solvent power.

The present invention derives in part from the observation that the highest levels of fouling are observed during the processing of 'dumb-bell' crude oil blends, i.e. mixtures of heavy and light crude oils that are blended together in the right proportions to produce an optimal refinery feed blend. However, such blends tend to contain high levels of paraffins. It has been noticed that blends rich in high levels of light paraffins are typically those that exhibit the highest levels of fouling. By looking at the light paraffin content of the hydrocarbon fluids, a more accurate relationship between fouling and the ratio of solvent power to critical solvent power may be determined and used to predict the fouling tendency of other hydrocarbon fluids.

DETAILED DESCRIPTION OF THE INVENTION

Subgrouping of Hydrocarbon Fluids

The plurality of hydrocarbon fluids are divided into subgroups, based on the ratio of solvent power to critical solvent power.

The plurality of hydrocarbon fluids may be divided into at least 3 subgroups, preferably at least 4 subgroups, and more preferably at least 5 subgroups. A greater number of subgroups will give a more accurate relationship between the ratio of solvent power to critical solvent power and the light paraffin content. However, this has to be offset against the benefits of having a larger number of hydrocarbon fluids within each subgroup.

Each subgroup may contain at least 2 hydrocarbon fluids, preferably at least 4 hydrocarbon fluids, and more preferably at least 8 hydrocarbon fluids.

Each of the subgroups may have a size of up to 0.1 ratio units, preferably up to 0.08 ratio units, and more preferably up to 0.05 ratio units. For example, where each subgroup has a size of 0.05 ratio units, a first subgroup may include ratios of solvent power to critical solvent power of greater than 1.075 and up to 1.125 (i.e. the 1.10 subgroup), a second subgroup may include ratios of greater than 1.125 and up to 1.175 (i.e. the 1.15 subgroup), a third subgroup may include ratios of greater than 1.175 and up to 1.225 (i.e. the 1.20 subgroup), and a fourth subgroup may include ratios of greater than 1.225 and up to 1.275 (i.e. the 1.25 subgroup).

Each subgroup may be the same size, but it does not have to be. For example, one subgroup may cover 0.03 ratio units (e.g. those hydrocarbon fluids having a ratio falling within the range 1.10-1.13) whilst another subgroup may cover 0.5 ratio units (e.g. those hydrocarbon fluids having a ratio falling within the range 1.13-1.18).

Solvent Power

The solvent power of the hydrocarbon fluid may be determined using any known method. For instance, the methodology described in US 2004/0121472 (Nemana, S. et al: Predictive Crude Oil Compatibility Model; incorporated herein by reference) may be used. According to this method, solvent power is estimated using the characterisation K factor.

The characterisation K factor, $K_{HF}$, is calculated according the following formula:

$$K_{HF} = VABP_{HF}^{1/3} / SG_{HF}$$

where: $VABP_{HF}$ is the volume average boiling point of the hydrocarbon fluid, in degrees Rankine, and
$SG_{HF}$ is the standard specific gravity of the hydrocarbon fluid.

The volume average boiling point of the hydrocarbon fluid, $VABP_{HF}$, may be determined using known methods. In some instances, $VABP_{HF}$ may be determined from the yield profile of the hydrocarbon fluid.

The yield profile of the hydrocarbon fluid may be determined from physical distillation, for instance according to ASTM D 2892 or ASTM D 5236. The yield profile of the hydrocarbon fluid may alternatively be determined using GC and high temperature simulated distillation (HT-SIMDIS). Use of GC analysis allows the hydrocarbon composition of the oil to be determined for components boiling in the $C_{1-9}$ hydrocarbon range. GC analysis may be carried out according to standard test method IP 601. HT-SIMDIS analysis may be carried out according to standard test method IP 545.

The standard specific gravity of the hydrocarbon fluid, $SG_{HF}$, is the ratio of the density of the hydrocarbon fluid to that of water at 60° F. (i.e. 15.6° C.). $SG_{HF}$ may be determined using known methods. For instance, as mentioned above, the density of the hydrocarbon fluid may be measured experimentally according to ASTM D 4052 or D 5002.

The solvent power of the hydrocarbon fluid, $SP_{HF}$, may be determined from the characterisation K factor using linear interpolation. For instance, $SP_{HF}$ may be determined from $K_{HF}$ based on the relationship between the characterisation K factor and the solubility parameter of heptane and toluene. The characterisation K factor and the solubility parameter of heptane and toluene are known in the art.

Critical Solvent Power

The critical solvent power of the hydrocarbon fluid, $CSP_{HF}$, may be determined by titrating the hydrocarbon fluid against a precipitant. In some instances, $CSP_{HF}$ may be determined according to the following formula:

$$CSP_{HF} = V_{(onset\ fraction\ HF)} * SP_{HF} / 100$$

where: $V_{(onset\ fraction\ HF)}$ is the volume fraction of the hydrocarbon fluid at the onset of asphaltene precipitation; and
$SP_{HF}$ is the solvent power of the hydrocarbon fluid, which may be determined as described above, e.g. based on the characterisation K factor.

The precipitant that is used for determining $CSP_{HF}$ preferably has a negligible solvent power, such as a solvent power of less than 5, and preferably less than 2. In some instances, the precipitant may have a solvent power of about 0. Suitable precipitants include alkanes, such as $C_{4-20}$ alkanes, and preferably $C_{4-20}$ n-alkanes or $C_{4-20}$ iso alkanes. In some instances, the precipitant is selected from heptane, undecane and pentadecane.

The hydrocarbon fluid and the precipitant may be equilibrated from 20 minutes to 40 minutes, such as 30 minutes. In some instances, the hydrocarbon fluid and the precipitant are undisturbed during this time, i.e. they are not subjected to any mixing or agitation. Titration intervals of less than 15% by volume, such as less than 10% by volume, and preferably less than 5% by volume may be used.

The hydrocarbon fluid and precipitant mixtures that may be prepared in order to determine $CSP_{HF}$ may be observed under an optical microscope to determine when asphaltene precipitation occurs. Alternatively, the mixtures may be subjected to centrifugation, with any solids washed (e.g. using the precipitant) and weighed to determine the amount of asphaltene precipitation.

Threshold Light Paraffin Content

Generally, the higher the content of light paraffins in a hydrocarbon fluid, the greater the fouling tendency of the hydrocarbon fluid. The threshold light paraffin content is the light paraffin content of the hydrocarbon fluids within a subgroup at the point at which the fouling tendency of the hydrocarbon fluids exceeds a fouling threshold.

The threshold light paraffin content may be determined by identifying the highest light paraffin content of those hydrocarbon fluids in the subgroup having a fouling tendency which falls below the fouling threshold.

Alternatively, a linear relationship between fouling tendency and light paraffin content may be modelled, e.g. using simple linear regression techniques. The light paraffin content of a hydrocarbon fluid at the point at which fouling tendency is equal to the fouling threshold may then be readily determined. This method is particularly useful if none of the hydrocarbon fluids in the subgroup have a fouling tendency which exceeds the fouling threshold.

Fouling Tendency

In some instances, information on the fouling tendency of a hydrocarbon fluid may be readily available. In other instances, the method defined herein comprises measuring the fouling tendency of the plurality of hydrocarbon fluids, e.g. using known methods.

The fouling tendency of the hydrocarbon fluids may be determined by subjecting the hydrocarbon fluid to conditions which simulate the effect of a refinery on the hydrocarbon fluids.

Typically, miniaturized experiments will be conducted so that a full scale refinery test is not required. A full scale refinery operation may be simulated in the miniaturized experiments. Accordingly, only a small amount of hydrocarbon fluid is required to carry out the simulation. In some instances, less than 10 L, and preferably less than 5 L, of each hydrocarbon fluid will be required for the test.

Experiments may comprise heating the hydrocarbon fluid and contacting the hydrocarbon fluid with a surface, such as a metal surface. The hydrocarbon fluid may be heated by the surface. This simulates the action of a heat exchanger on a hydrocarbon fluid in a full scale refinery.

The conditions under which fouling tests are carried out may vary to reflect the conditions in different refineries.

For example, the hydrocarbon fluid may be contacted with the surface which is heated to a temperature of from 200 to 800° C., such as from 250 to 600° C.

The hydrocarbon fluid may be contacted with the surface for a time period of from 15 minutes to 24 hours, such as from 30 minutes to 15 hours, and preferably from 2 to 10 hours, The hydrocarbon fluid may be passed over the surface at a rate of from 0.1 to 20 $cm^3$/minute, such as from 0.5 to 10 $cm^3$/minute.

The surface with which the hydrocarbon fluid is contacted may be a metal tube, e.g. around which the hydrocarbon fluid flows, or a flat surface.

The fouling tendency of a fluid may be determined by measuring the mass of the deposits produced by the hydrocarbon fluid, or by looking at the change in heat exchange with the hydrocarbon fluid as a result of deposits from the fluid.

Where the hydrocarbon fluid is contacted with a surface, the surface may be weighed after the test has been completed to determine the mass gain. Where the surface is used to heat the hydrocarbon fluid, the temperature of the hydrocarbon fluid along the surface may be measured during the test, to determine the temperature changes that are observed as a result of deposit build up. For instance, the temperature of the hydrocarbon fluid may be measured before and after contact with the surface. As more deposits build up on the surface, the heat transfer to the hydrocarbon fluid will worsen and a reduction in the difference between the temperature of the hydrocarbon fluid before and after contact with the surface will be observed.

In some instances, the fouling tendency of a hydrocarbon fluid may be determined by carrying out hot liquid process simulator (HLPS) tests, e.g. on an Alcor fouling Unit. The HLPS is a simplified heat exchanger, which may consist of an electrically heated metal tube (typically carbon steel) placed within a cylindrical housing. The tubes may be disposable, so that a fresh tube may be used for each experiment. Tubes may be weighed at the start of each experiment. The hydrocarbon fluid flows over the annular space that is present between the heated tube and the cylindrical housing. A constant tube wall temperature may be maintained.

In an HLPS test, the surface of the tube is initially clean and heat transfer efficiency is high. This results in a rapid increase in the hydrocarbon fluid temperature across the length of heated section, resulting in a steady (and high) outlet temperature. A maximum may be reached 10 to 15 minutes into the experiment. If the asphaltenes precipitate from the hydrocarbon fluid and deposit on the surface of the electrically heated tube, a decrease in heat transfer efficiency is observed. This translates into a lower fluid outlet temperature over time. The total decrease in outlet temperature over the course of a typical run can be used as a means to assess fouling tendency for different feeds.

At the end of an experiment, the heater tube may be removed from the housing, rinsed in a solvent (e.g. petroleum ether), dried and weighed. The change in mass of the tube during the experiment may be recorded, and the mass gain used as an indicator for fouling tendency.

By adjusting the HLPS test conditions (e.g. varying the feed flowrate, system pressure, wall temperature, inlet temperature, etc.), relationships between the ratio of solvent power to critical solvent power and the threshold light paraffin content of hydrocarbon fluids under a variety of different conditions, e.g. which reflect those found at different refineries, may be determined.

Fouling Threshold

Oils having a fouling tendency which falls at or below a fouling threshold are deemed to be suitable for use in a refinery. Accordingly, the fouling threshold should be selected to meet the requirements of a full scale refinery in which the hydrocarbon fluid may be used. The fouling threshold may vary according to a number of different factors. For instance, some refineries may be able to withstand greater degrees of fouling than other refineries.

The threshold for fouling will be predetermined, rather than dependent on the outcome of the fouling tests for the hydrocarbon fluid. The fouling threshold is generally predetermined using operating experience at a particular refinery or refineries. For instance, one or more feedstocks which are known to produce low, acceptable or high fouling rates in a refinery may be tested, e.g. in the HLPS unit, to determine the fouling tendency, e.g. mass gain or temperature change, for each feedstock. The fouling tendency of hydrocarbon fluids may then be measured, and ranked relative to the one or more feedstocks which are known to produce low, acceptable or high fouling rates.

In instances where fouling tendency is determined using HLPS methods, then an appropriate fouling threshold for a standard refinery may be those hydrocarbon fluids which have a low fouling tendency (i.e. hydrocarbon fluids which have a ΔT of greater than 25° C. or a mass gain of greater than 30 mg fall above the fouling threshold as their fouling tendency is too high for use in a refinery):

| Fouling threshold | ΔT (° C.) | | Mass Gain (mg) |
|---|---|---|---|
| Low | ≤25 | or | ≤30 |
| Moderate | ≤40 | or | ≤50 |

In other instances where fouling tendency is determined using HLPS methods, then an appropriate threshold for fouling tendency may be a moderate fouling threshold.

Light Paraffin Content

The light paraffin content of the hydrocarbon fluid may be measuring using GC analysis, e.g. according to the method defined in IP 601 or equivalent. Alternatively, the content of different paraffins in the hydrocarbon fluid may be readily obtained from assay data on the hydrocarbon fluid.

The cut-off point for a paraffin to be considered a 'light paraffin' is not crucial. Preferably, any measure of light paraffin content would include at least the $C_{1-4}$ paraffins, and would exclude any $C_{13+}$ (i.e. $C_{13}$ and higher) paraffins.

It is believed that accurate results are obtained by looking at the total content of light distillates in the hydrocarbon fluid. Light distillates typically include liquid petroleum gas (LPG), gasoline, heavy naphtha and light naphtha. Light distillates may be categorized as those components boiling below a temperature of 150° C., e.g. as measured according to ASTM D 2892 or IP 545, preferably ASTM D 2892.

Accurate results may also be obtained by determining the light paraffin content by looking at the $C_{1-4}$, $C_{1-5}$, $C_{1-6}$, $C_{1-7}$, $C_{1-8}$, $C_{1-9}$ or $C_{1-10}$ paraffin content of the hydrocarbon fluid. Preferably, the light paraffin content is determined by measuring the $C_{1-5}$ or $C_{1-8}$ paraffin content, in particular the $C_{1-8}$ paraffin content, of the hydrocarbon fluid. The $C_{1-4}$, $C_{1-5}$, $C_{1-6}$, $C_{1-7}$, $C_{1-8}$, $C_{1-9}$ or $C_{1-10}$ paraffin content may be determined according to method IP 601.

Determining a Relationship

Once the threshold light paraffin content has been determined for each of the subgroups of hydrocarbon fluids, then a relationship between the ratio of solvent power to critical solvent power and the threshold light paraffin content may be determined.

Each of the subgroups of hydrocarbon fluids has a threshold light paraffin content. The threshold light paraffin content will generally be associated with a value which represents the ratio of solvent power to critical solvent power for the subgroup. This value will generally fall in the centre of the subgroup. For example, where the subgroup includes ratios of greater than 1.075 and up to 1.125, the ratio which is associated with the threshold light paraffin content will be 1.10 subgroup. However, in some cases, e.g. where the data is unevenly distributed, the value may be the average (e.g. mean or median) ratio of solvent power to critical solvent power of all of the hydrocarbon fluids falling within the subgroup. In other cases, e.g. where a conservative relationship is desired, the value may be the highest ratio of solvent power to critical solvent power which a hydrocarbon fluid may take to fall within the subgroup.

The relationship between the ratio of solvent power to critical solvent power and the threshold light paraffin content is believed to be largely linear in nature. Accordingly, the relationship may be modelled, e.g. using simple linear regression techniques.

Other Aspects

Once a relationship between the ratio of solvent power to critical solvent power and the threshold light paraffin content has been determined, it may be used in a method for predicting the ratio of solvent power to critical solvent power at which a hydrocarbon fluid will fall below a fouling threshold for a particular light paraffin content.

The relationship may also be used in a method for determining whether a hydrocarbon fluid will exhibit an acceptable level of fouling. Such a method comprises (a) determining the ratio of solvent power to critical solvent power and the light paraffin content of the hydrocarbon fluid; (b) based on the light paraffin content of the hydrocarbon fluid, predicting the ratio of solvent power to critical solvent at which the hydrocarbon fluid will fall below a fouling threshold using a relationship determined using a method disclosed herein; and (c) comparing the ratio determined in step (a) with the ratio predicted in step (b) in order to determine whether the hydrocarbon fluid will exhibit an acceptable level of fouling.

This information may be used in methods for reducing the precipitation of asphaltenes in a refinery. Where the ratio determined in step (a) is greater than or equal to the ratio predicted in step (b), then the risk of asphaltene fouling is low, and the hydrocarbon fluid may be passed to a refinery. Where the ratio determined in step (a) is less than the ratio predicted in step (b), then the risk of asphaltene fouling is higher. Thus, where the ratio determined in step (a) is less than the ratio predicted in step (b), the method may comprise further blending of the crude oil to increase the ratio of solvent power to critical solvent power.

Asphaltene precipitation may be reduced in at least one of the heat exchangers and the furnace. Preferably, asphaltene precipitation is reduced on the surface of the heat exchangers in the refinery.

Hydrocarbon Fluid

The hydrocarbon fluids may have originated from a subterranean formation, and undergone subsequent treatment to remove any excessive gas content and other contaminants. Preferably, each of the hydrocarbon fluids is a crude oil or a blend of crude oils.

Hydrocarbon fluids which are a blend of crude oils are typically found in refineries which process a range of crude oils, e.g. originating from different regions in the world, with different physical properties, e.g. density, sulphur content, type and amount of light paraffins, solvent power etc. Some refineries process from 2-20 different crude oils at any time. These crude oils are typically blended together before processing. In some instances, the crude oils may be blended together in a refinery to produce dumb-bell crude blends, i.e. crude oil blends of a relatively heavy crude oil and a relatively light crude oil, such as blends of a crude oil having an API gravity of greater than 35° and a crude oil having an API gravity of less than 25°, e.g. as measured according to ASTM D 4025. As discussed herein, dumb-bell crude oils have been found to be particularly prone to fouling. Accordingly, in some instances of the present invention, the hydrocarbon fluid used in the present invention is a dumb-bell crude blend.

In some embodiments, the hydrocarbon fluid is a crude oil which has a fouling tendency which falls around the fouling threshold. In some instances, the hydrocarbon fluid has a fouling tendency which falls within a range of the fouling threshold±30%, such as the fouling threshold±20%, and preferably the fouling threshold±10%. In these embodiments, hydrocarbon fluids having a high fouling tendency are discounted for use in a refinery until they are further blended with a hydrocarbon fluid to reduce the fouling tendency. Similarly, hydrocarbon fluids which exhibit a low fouling tendency are considered suitable for use in a refinery without any further experimentation.

Accordingly, in some embodiments, the method of determining a relationship between the ratio of solvent power to critical solvent power and the threshold light paraffin content involves a step of limiting the plurality of hydrocarbon fluids to those that have a fouling tendency which falls around the fouling threshold.

Figure 1:
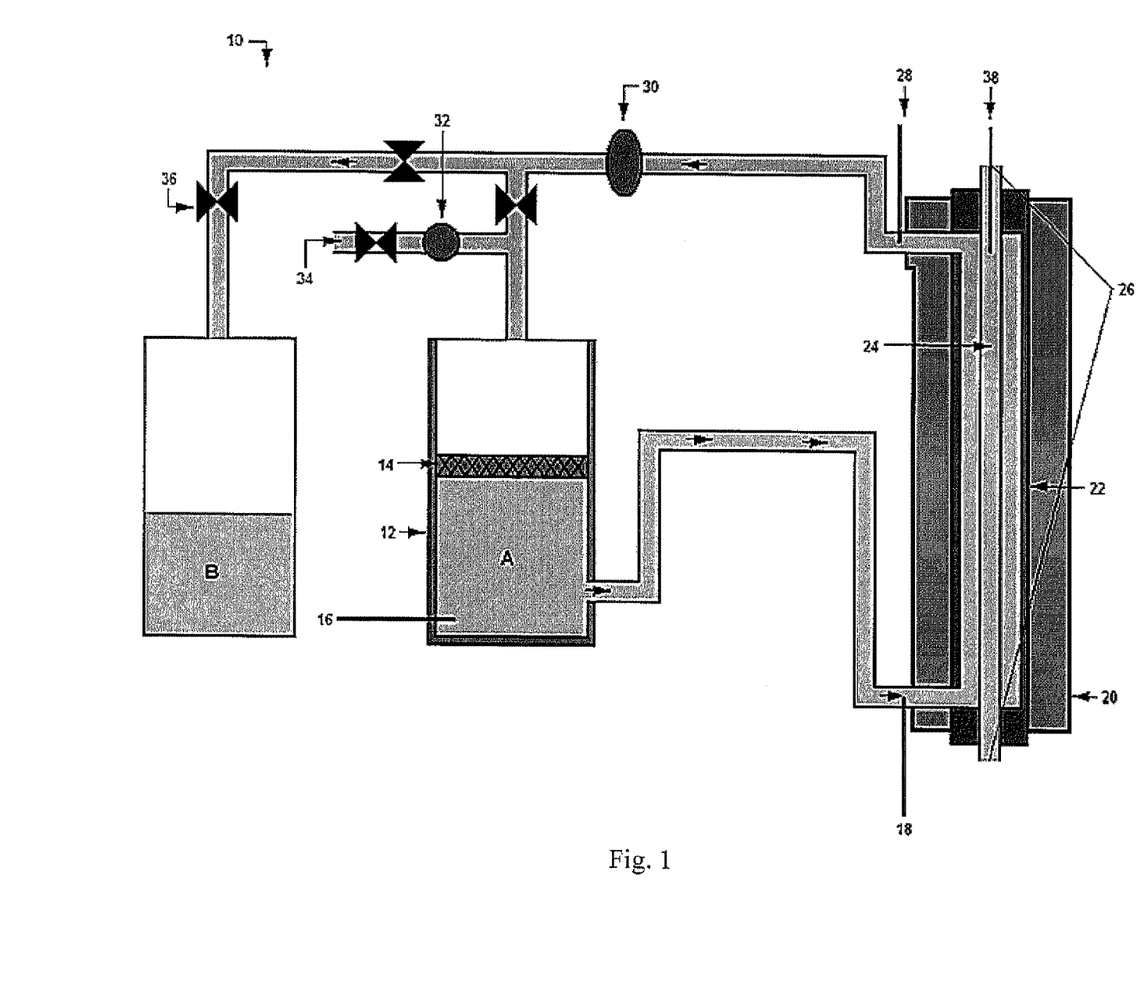
FIG. 1 is a diagram of an HLPS that may be used to test the fouling tendency of a hydrocarbon fluid.

The invention will now be described with reference to the accompanying figures and examples, in which:

FIG. 1 shows a diagram of an HLPS (10) that may be used to test the fouling tendency of a hydrocarbon fluid. The hydrocarbon fluid to be tested (A) is held in a heated tank (12) capped with a floating seal (14). The fluid is passed to a simplified heat exchanger which comprises a heated tube (24) and a metal housing (22) which define an annular space. The metal housing (22) is surrounded by insulation (20). Electrical power (26) provides the heat for the heated tube (24). As the fluid passes through the annular space, it is heated up. Thermocouples (16, 18, 28, 38) measure the heat at various points in the system. On leaving the annular space, the hydrocarbon fluid passes through a speed monitoring pump (30). The spent fluid (B) may be passed to a storage tank, with valves (e.g. 36) controlling the route of the fluid. A pressure gauge (32) and nitrogen inlet (34) control the pressure in the system.

EXAMPLES

Example 1: Testing the Fouling Threshold of Crude Oils 137 typical crude oil dumb-bell blends were created and subjected to testing using an Alcor HLPS unit as shown in FIG. 1. A fresh heated tube was used for each experiment. The tubes were weighed at the start of each experiment. A constant temperature was maintained along the tube wall.

The conditions used in the Alcor unit fell within typical test conditions:

Feed Inlet Temperature: 20-100° C.
Wall temperature: 350-500° C.
Oil Flowrate: 1-5 cm$^3$/min
Test duration: 3-8 hours
Pressure: 300-820 psig The hydrocarbon fluids exited the annular space surrounding the heated tube at temperatures falling within the range of 250-400° C.

Initially during each experiment, the surface of the tube was clean and heat transfer efficiency was high. This resulted in a rapid increase in the feed temperature across the length of heated section, resulting in a steady and relatively high outlet temperature. A maximum outlet temperature was typically reached 10-15 minutes into the experiment. Asphaltene precipitated from the hydrocarbon fluid and deposited on the surface of the heated tube, causing a decrease in heat transfer efficiency. This translated into a lowering of the outlet temperature over time. The total decrease in outlet temperature over the course of the run, was used as a means to assess fouling rates for different feeds.

At the end of the experiment, the heated tube was removed from the unit, rinsed, dried and weighed. The change in mass of the tube was recorded and also used as an indicator for fouling rates.

Figure 2:
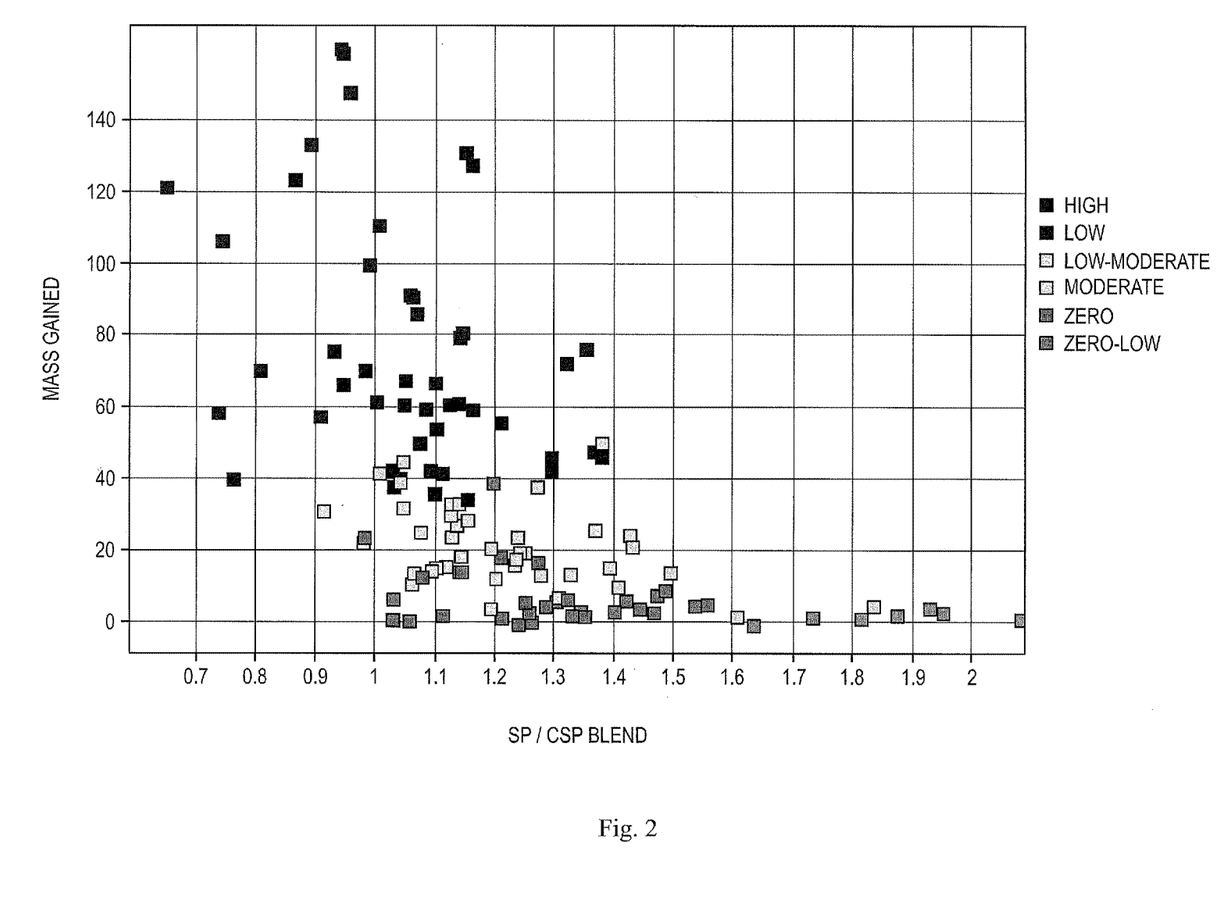
FIG. 2 shows a graph of mass gained against ratio of solvent power to critical solvent power for 137 dumb-bell crude oil blends.

The feedstocks were assigned a fouling tendency of high, moderate, moderate-low, low, low-zero and zero based on the temperature change during the experiments. FIG. 2 shows a graph of mass gained against ratio of solvent power to critical solvent power. The entries on the graph are shaded to show the fouling tendency as measured using temperature change.

It can be seen from the graph that the general trend is for the fouling tendency of the hydrocarbon feedstock to decrease as the ratio of solvent power to critical solvent power increase. However, some feedstocks exhibit a high fouling tendency in spite of a relatively high ratio of solvent power to critical solvent power, and some feedstocks exhibit a low fouling tendency in spite of a relatively low ratio of solvent power to critical solvent power.

Example 2: Determining a Relationship Between the Ratio of Solvent Power to Critical Solvent Power and the Threshold Light Paraffin Content Further investigation of the blend properties of the feedstocks resulted in the finding that the blends with an unexpectedly high fouling tendency were typically rich in light components, i.e. material boiling at <150° C.

The feedstocks were divided into 4 subgroups based on the ratio of solvent power to critical solvent power:

| Subgroup | Ratio of solvent power to critical solvent power (R) |
| --- | --- |
| 1.10 | $1.075 < R \leq 1.125$ |
| 1.15 | $1.125 < R \leq 1.175$ |
| 1.20 | $1.175 < R \leq 1.225$ |
| 1.25 | $1.225 < R \leq 1.275$ |

The fouling threshold was set at a mass gain of 30 mg.

Figure 3A:
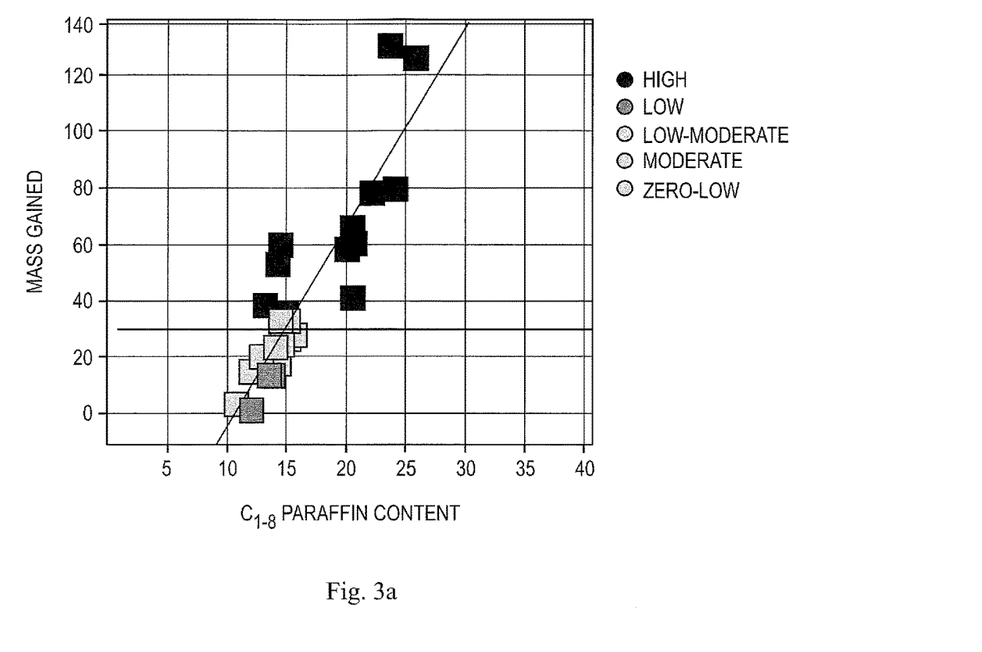
FIGS. 3a and 3b show graphs of mass gain against light paraffin content for subgroups of the dumb-bell crude oil blends having a ratios of solvent power to critical solvent power of around 1.15 and 1.20, respectively.
Figure 3B:
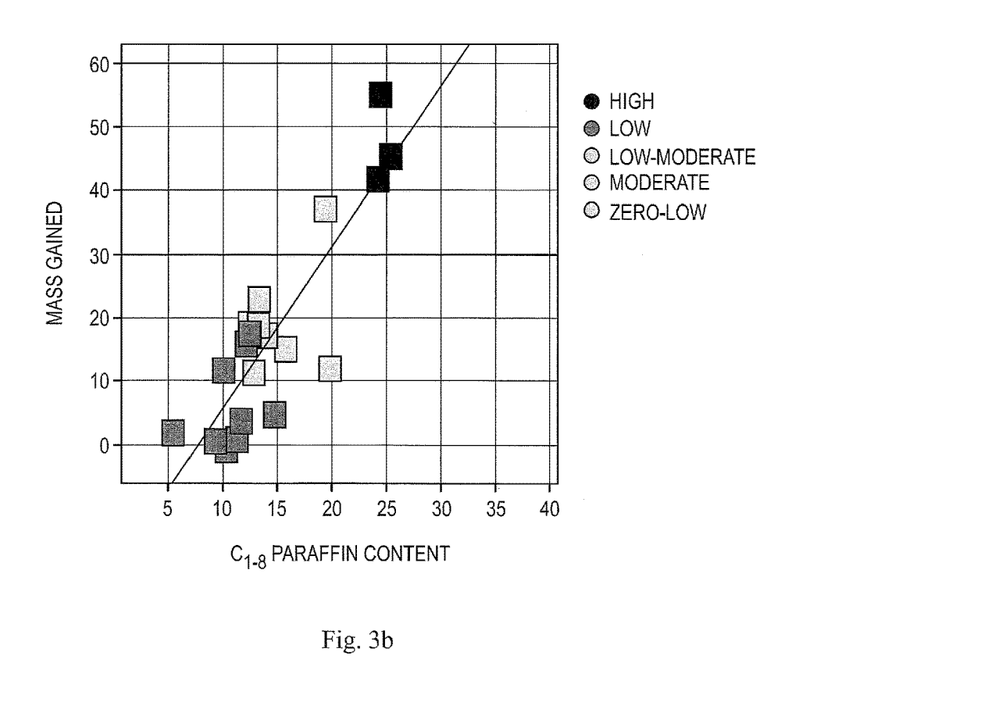

Graphs of mass gain against light paraffin content (% by volume) were plotted and a linear relationship determined. Graphs for the 1.15 ratio subgroup and the 1.20 ratio subgroup are shown in FIGS. 3a and 3b. The threshold paraffin content can be deduced from the graphs as the point at which a line showing the fouling threshold intersects a line plotting the relationship between mass gain and light paraffin content. It can be seen from FIGS. 3a and 3b that the threshold paraffin content for the 1.15 ratio subgroup is approximately 15% by volume, whereas the threshold paraffin content for the 1.20 ratio subgroup is approximately 20% by volume.

Figure 4:
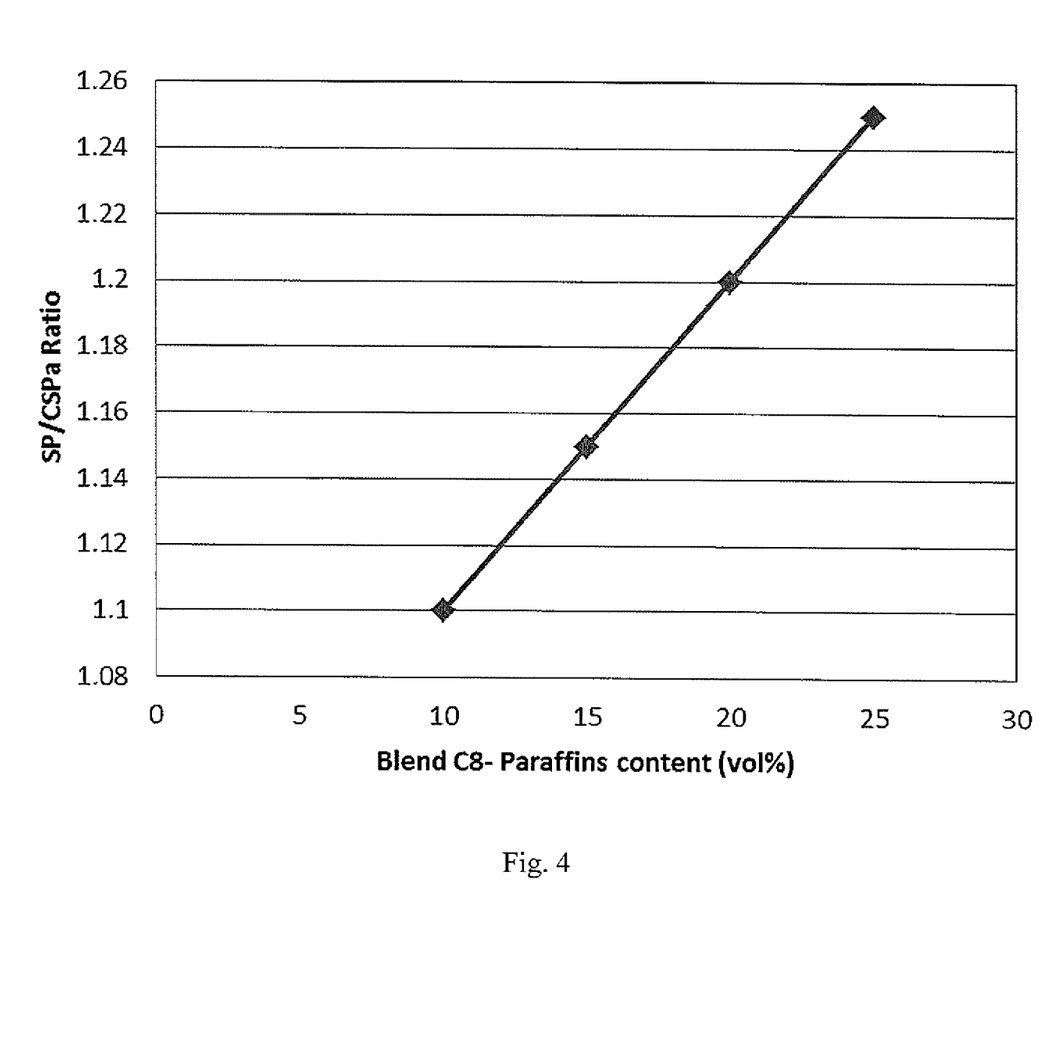
FIG. 4 shows a graph of ratio of solvent power to critical solvent power against threshold $C_{1-8}$ paraffin content for crude oil blends.

The minimum ratio of solvent power to critical solvent power required for adequate fouling levels for blends with varying paraffins content (by volume) was determined. The following guidelines were established:

$C_{1-8}$ content≤10%: a ratio as low as 1.05-1.1 may be acceptable;
10%<$C_{1-8}$ content≤15%: a ratio of 1.15 or higher is preferred;
15%<$C_{1-8}$ content≤20%: a ratio of 1.15-1.20 or higher is preferred; and
25%<$C_{1-4}$ content: very high ratios (>1.25) may be required A linear relationship between threshold $C_{1-8}$ paraffin content and the ratio of solvent power to critical solvent power was determined as is shown in graph form in FIG. 4. The following relationship was deduced:

Minimum ratio of solvent power to critical solvent power required=1+0.01 ($C_{1-8}$ paraffins content, vol %) for acceptable fouling levels The ratio of solvent power to critical solvent power of a crude oil or a crude oil blend may be compared to the minimum ratio as defined by the equation above to determine whether it will exhibit acceptable fouling rates.

The invention claimed is:

1. A method for reducing the precipitation of asphaltene from a hydrocarbon fluid in a refinery, said method comprising:
   (a) measuring the ratio of solvent power to critical solvent power and the light paraffin content of the hydrocarbon fluid;
   (b) based on the light paraffin content of the hydrocarbon fluid, predicting the ratio of solvent power to critical solvent power at which the hydrocarbon fluid will fall below a fouling threshold; and
   (c) comparing the ratio measured in step (a) with the ratio predicted in step (b) to determine whether the hydrocarbon fluid will exhibit an acceptable level of fouling; and
   (d) feeding the hydrocarbon fluid to the refinery if the ratio of solvent power to critical solvent power is (i) about 1.05 to about 1.1 when the $C_{1-8}$ content is less than or equal to 10% or (ii) at least about 1.15 when the $C_{1-8}$ content greater than 10% but less than or equal to 20% or (iii) greater than about 1.25 when the $C_{1-8}$ content is greater than 25% and, if not, further blending the hydrocarbon fluid with different crude oils together in a refinery to produce a dumb-bell crude blend to increase the ratio of solvent power to critical solvent power.

2. The method of claim 1, wherein predicting the ratio of solvent power to critical solvent power at which the hydrocarbon fluid will fall below a fouling threshold comprises the steps of:
   (a) dividing a plurality of hydrocarbon fluids into subgroups, based on the ratio of solvent power to critical solvent power;
   (b) for each of the subgroups, determining threshold light paraffin content said threshold light paraffin content being the light paraffin content of the hydrocarbon fluids at the point at which fouling tendency of the hydrocarbon fluids exceeds a fouling threshold; and
   (c) measuring the ratio of solvent power to critical solvent power and the threshold light paraffin content;
   (d) predicting the ratio of solvent power to critical solvent power at which the hydrocarbon fluid will fall below a fouling threshold based on the light paraffin content of the hydrocarbon fluid; and
   (e) comparing the ratio measured in step (c) with the ratio predicted in step (b) in order to determine whether the hydrocarbon fluid will exhibit an acceptable level of precipitation of asphaltene on the surface of heat exchangers in the refinery.

3. The method of claim 2, wherein the fluid is divided into at least 3 subgroups.

4. The method of claim 2, wherein each subgroup contains at least 2 hydrocarbon fluids.

5. The method of claim 2, wherein each of the subgroups has a size of up to 0.1 ratio units.

6. The method of claim 2, wherein the method comprises measuring the fouling tendency of the hydrocarbon fluids.

7. The method of claim 6, wherein the fouling tendency of the hydrocarbon fluids are determined by carrying out hot liquid process simulator tests.

8. The method of claim 2, wherein the light paraffin content of the hydrocarbon fluids is taken to be the light distillates content of the hydrocarbon fluid.

9. The method of claim 2, wherein the light paraffin content of the hydrocarbon fluid is taken to be the c1-4, c1-5, c1-6, c1-7, c1-8, c1-9 or c1-10 paraffin content of the hydrocarbon fluid.

10. The method of claim 2, wherein the method comprises measuring the solvent power of the hydrocarbon fluids.

11. The method of claim 10, wherein the solvent power of the hydrocarbon fluids is estimated using characterisation K factor.

12. The method of claim 2, wherein the method comprises measuring the critical solvent power of the plurality of hydrocarbon fluids.

13. The method of claim 12, wherein the critical solvent power of the hydrocarbon fluids is measured by titrating the hydrocarbon fluids against a precipitant.

14. The method of claim 2, wherein the hydrocarbon fluids are crude oils or blends of crude oils.

15. The method of claim 14, wherein the blends of crude oil are blends of a relatively heavy crude oil and a relatively light crude oil.

16. The method of claim 1, wherein the precipitation of asphaltene is reduced on the surface of heat exchangers in the refinery.

* * * * *